United States Patent
Bangel et al.

(10) Patent No.: US 9,854,800 B2
(45) Date of Patent: Jan. 2, 2018

(54) HERBICIDAL COMPOSITIONS COMPRISING 4-AMINO-3-CHLORO-6-(4-CHLORO-2-FLUORO-3-METHOXYPHENYL)-5-FLUOROPYRIDINE-2-CARBOXYLIC ACID OR A DERIVATIVE THEREOF AND CHLORMEQUAT CHLORIDE

(71) Applicant: Dow AgroSciences LLC, Indianapolis, IN (US)

(72) Inventors: Bryston L. Bangel, Camby, IN (US); Norbert M. Satchivi, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/215,972

(22) Filed: Jul. 21, 2016

(65) Prior Publication Data

US 2017/0020133 A1    Jan. 26, 2017

Related U.S. Application Data

(60) Provisional application No. 62/196,356, filed on Jul. 24, 2015.

(51) Int. Cl.
*A01N 43/40* (2006.01)

(52) U.S. Cl.
CPC .................................. *A01N 43/40* (2013.01)

(58) Field of Classification Search
None
See application file for complete search history.

(56) References Cited

U.S. PATENT DOCUMENTS 7,314,849 B2 *    1/2008  Balko .................... A01N 43/40
                                                            504/244

* cited by examiner

*Primary Examiner* — Alton Pryor
(74) *Attorney, Agent, or Firm* — Michael R. Asam

(57) ABSTRACT

Provided herein are herbicidal compositions comprising (a) 4-amino-3-chloro-6-(4-chloro-2-fluoro-3-methoxyphenyl)-5-fluoropyridine-2-carboxylic acid or an agriculturally acceptable salt or ester thereof and (b) chlormequat chloride and methods of use. The compositions provide control of undesirable vegetation in crops such as cereal crops, like wheat and barley.

19 Claims, No Drawings

HERBICIDAL COMPOSITIONS COMPRISING 4-AMINO-3-CHLORO-6-(4-CHLORO-2-FLUORO-3-METHOXYPHENYL)-5-FLUOROPYRIDINE-2-CARBOXYLIC ACID OR A DERIVATIVE THEREOF AND CHLORMEQUAT CHLORIDE

CROSS REFERENCE TO RELATED APPLICATIONS

This application claims the benefit of U.S. Provisional Patent Application Ser. No. 62/196,356 filed Jul. 24, 2015, which is expressly incorporated by reference herein.

BACKGROUND

The inhibition of crop growth by impingement from weeds and other vegetation is a recurring problem in agriculture. To help combat this problem, a variety of chemicals and chemical formulations effective in the control of such unwanted vegetation have been synthesized and evaluated. Different classes of chemical herbicides have been disclosed in the literature and a large number are in commercial use.

SUMMARY

Compositions for controlling undesirable vegetation comprising a herbicidally effective amount of (a) a compound of the formula (I)

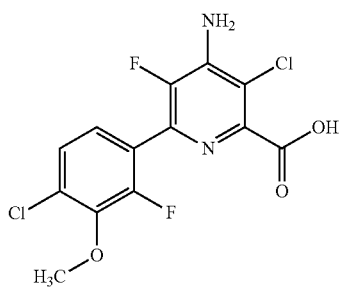

(I)

or an agriculturally acceptable salt or ester of thereof and (b) chlormequat chloride are described herein.

Additionally, methods of controlling undesirable vegetation including contacting the vegetation or the locus thereof, including but not limited to, soil or water, with a composition containing a herbicidally effective amount of (a) a compound of the formula (I) or an agriculturally acceptable salt or ester thereof and (b) chlormequat chloride to prevent the emergence or growth of vegetation, particularly undesirable vegetation are described herein.

DETAILED DESCRIPTION

Definitions

As used herein, the compound of formula (I) is 4-amino-3-chloro-6-(4-chloro-2-fluoro-3-methoxyphenyl)-5-fluoropyridine-2-carboxylic acid and has the following structure:

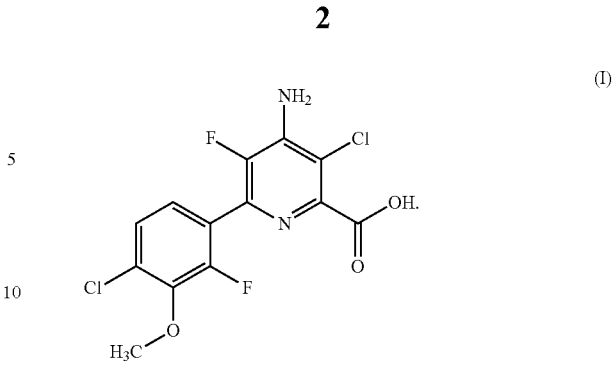

(I)

Compounds of formula (I) are described in U.S. Pat. No. 7,314,849 B2, which is incorporated herein by reference in its entirety. Exemplary uses of the compound of the formula (I), which is also known as Rinskor™ active and florpyrauxifen, include controlling undesirable vegetation, including grass, broadleaf and sedge weeds, in multiple non-crop and cropping situations.

Exemplary chemical forms of the compound of formula (I) include, but are not limited to, for example, the benzyl ester of the compound of formula (I), florpyrauxifen-benzyl, or benzyl 4-amino-3-chloro-6-(4-chloro-2-fluoro-3-methoxyphenyl)-5-fluoropyridine-2-carboxylate and has the following structure:

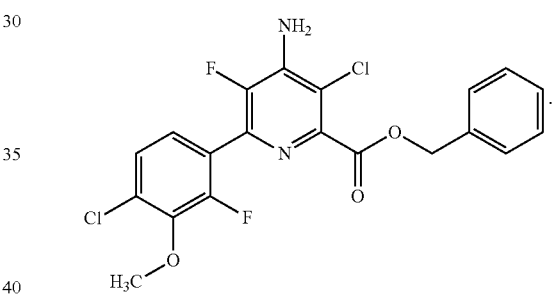

The benzyl ester form of formula (I) is described in U.S. Pat. No. 8,883,688 B2, which is incorporated herein by reference in its entirety.

As used herein, chlormequat chloride is (2-chloroethyl)trimethylammonium chloride or 2-chloro-N,N,N-trimethylethanaminium chloride, which has the following structure:

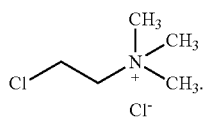

Chlormequat chloride is described in Tomlin, C. D. S., Ed. *The Pesticide Manual: A World Compendium*, 15$^{th}$ ed.; BCPC: Alton, 2009 (hereafter "*The Pesticide Manual*, Fifteenth Edition, 2009"). Chlormequat chloride is used to increase lodging by shortening and strengthening the stem of the plant and to increase yields in wheat, rye, oats, and triticale.

The term herbicide, as used herein, means an active ingredient that kills, controls or otherwise adversely modifies the growth of plants. As used herein, a herbicidally effective or vegetation controlling amount is an amount of active ingredient which causes a "herbicidal effect," .i.e. an adversely modifying effect and includes deviations from natural development, killing, regulation, desiccation, retardation.

As used herein, controlling undesirable vegetation means preventing, reducing, killing, or otherwise adversely modifying the development of plants and vegetation.

As used herein, plants and vegetation include, but are not limited to, germinant seeds, emerging seedlings, plants emerging from vegetative propagules, and established vegetation.

As used herein, agriculturally acceptable salts and esters refer to salts and esters that exhibit herbicidal activity or that are or can be converted in plants, water, or soil to the referenced herbicide or active moiety. Exemplary agriculturally acceptable esters are those that are or can be hydrolyzed, oxidized, metabolized, or otherwise converted, e.g., in plants, water, or soil, to the corresponding carboxylic acid which, depending upon the pH, may be in the dissociated or undissociated form.

Exemplary salts include those derived from alkali or alkaline earth metals and those derived from ammonia and amines Exemplary cations include sodium, potassium, magnesium, and aminium cations of the formula:

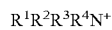

wherein $R^1$, $R^2$, $R^3$ and $R^4$ each, independently represents hydrogen or $C_1$-$C_{12}$ alkyl, $C_3$-$C_{12}$ alkenyl, $C_3$-$C_{12}$ alkynyl, or aryl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methyl-thiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions

Provided herein are herbicidal compositions containing a herbicidally effective amount of (a) a compound of the formula (I)

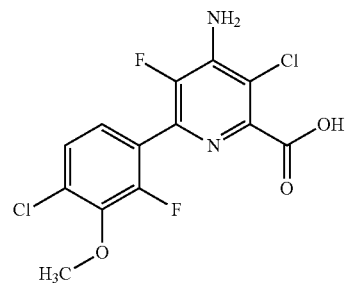

or an agriculturally acceptable salt or ester of thereof, and (b) chlormequat chloride.

In the compositions and methods described herein, the compound of formula (I), i.e., the carboxylic acid, is used. Alternatively, a carboxylate salt of the compound of formula (I) can be used, or an arylalkyl or alkyl ester can be used. Additionally, a benzyl, substituted benzyl, or $C_1$-$C_4$ alkyl, e.g., n-butyl ester can be used. In certain embodiments, the benzyl ester is employed.

The combination of a compound of formula (I) or agriculturally acceptable salt or ester thereof and chlormequat chloride can exhibit synergism, e.g., the herbicidal active ingredients are more effective in combination than when applied individually. Synergism has been defined as "an interaction of two or more factors such that the effect when combined is greater than the predicted effect based on the response of each factor applied separately." Shaner, D. L., Ed. *Herbicide Handbook*. $10^{th}$ ed. Lawrence: Weed Science Society of America, 2014. In certain embodiments, the compositions exhibit synergy as determined by the Colby equation (Colby, S. R. Calculation of the synergistic and antagonistic response of herbicide combinations. *Weeds* 1967, 15, 20-22).

Herbicidal activity is exhibited by the herbicidal compositions described herein when they are applied pre- and post-emergence directly to a plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, the amount of chemical applied, and combinations thereof. These and other factors can be adjusted to promote non-selective or selective herbicidal action. The compositions described herein can be applied as a post-emergence application, pre-emergence application, or in-water application to flooded paddy rice or water bodies (e.g., ponds, lakes and streams), to relatively immature to mature undesirable vegetation to achieve the maximum control of weeds.

The compound of formula (I) or salt or ester thereof and chlormequat chloride can be used in combination with herbicides that are selective for the crop being treated and complement the spectrum of weeds controlled by these compounds at the application rate employed. The compositions described herein and other complementary herbicides can be applied at the same time, either as a combination formulation, as a tank-mix, or as sequential applications.

The present compositions can be applied to vegetation or the soil or water adjacent thereto by the use of conventional ground or aerial dusters, sprayers, and granule applicators, by addition to irrigation or paddy water, and by other conventional means known to those skilled in the art.

The concentration of active ingredients in the compositions described herein is generally from 0.0005 to 98 percent by weight. Alternatively, the concentration can be from 0.0006 to 90 percent by weight. In compositions designed to be employed as concentrates, the active ingredients can be present in a concentration from 0.1 to 98 weight percent, or from about 0.5 to 90 weight percent. Such compositions can be diluted with an inert carrier, such as water, before application. The diluted compositions usually applied to weeds or the locus of weeds can contain about 0.0006 to 15.0 weight percent or from 0.001 to 10.0 weight percent active ingredient.

In the compositions and methods described herein, the weight ratio of the compound of formula (I) or salt or ester thereof to the chlormequat chloride on a gram active ingredient per hectare (g ai/ha) basis is within the range of from 1:1600 to 200:1. The weight ratio of the compound of formula (I) or salt or ester thereof to chlormequat chloride on a gram active ingredient per hectare (g ai/ha) basis also can be within the range from 1:1400 to 185:1, 1:1200 to 175:1, 1:1120 to 167:1, 1:1000 to 150:1, 1:750 to 130:1, 1:500 to 120:1, 1:447 to 112:1, 1:350 to 90:1, 1:250 to 70:1, 1:200 to 50:1, 1:175 to 40:1, 1:150 to 35:1, 1:112 to 28:1, 1:95 to 25:1, 1:85 to 20:1, 1:80 to 15:1, 1:75 to 12:1, 1:50 to 10:1, 1:40 to 8:1, 1:35 to 6.25:1, 1:32 to 5:1, 1:30 to 4.5:1, 1:28 to 4:1, 1:25 to 3.125:1.

The application rate will depend upon the particular type of weed to be controlled, the degree of control required, and the timing and method of application. In the compositions described herein the compound of formula (I) or salt or ester thereof can be applied at an application rate of from 1 gram active ingredient per hectare (g ai/ha) to 64 g ai/ha based on the total amount of the compound of formula (I) or salt or ester thereof in the composition. Additionally, in the compositions described herein the compound of formula (I) or salt or ester thereof can be applied at an application rate of from 1 g ai/ha to 60 g ai/ha, 2 g ai/ha to 50 g ai/ha, 2.5 g ai/ha to 45 g ai/ha, 1 g ai/ha to 50 g ai/ha, 2 g ai/ha to 45 g ai/ha, 2.5 g ai/ha to 40 g ai/ha, 5 g ai/ha to 60 g ai/ha, 5 g ai/ha to 50 g ai/ha, 1 g ai/ha to 45 g ai/ha, 1 g ai/ha to 40 g ai/ha, 1 g ai/ha to 35 g ai/ha, 1 g ai/ha to 25 g ai/ha, 2 g ai/ha to 20 g ai/ha, or 2.5 g ai/ha to 10 g ai/ha based on the total amount of the compound of formula (I) or salt or ester thereof in the composition. In the compositions described herein the chlormequat chloride can be applied at an application rate of from 1 g ai/ha to 1600 g ai/ha. Additionally, in the compositions described herein the chlormequat chloride can be applied at an application rate of from 1 g ai/ha to 1150 g ai/ha, 1 g ai/ha to 1120 g ai/ha, 1 g ai/ha to 1100 g ai/ha, 1 g ai/ha to 1000 g ai/ha, 1 g ai/ha to 800 g ai/ha, 1 g ai/ha to 600 g ai/ha, 250 g ai/ha to 1200 g ai/ha, 250 g ai/ha to 1120 g ai/ha, 275 g ai/ha to 1100 g ai/ha, 275 g ai/ha to 1000 g ai/ha, 275 g ai/ha to 800 g ai/ha, 275 g ai/ha to 600 g ai/ha, 275 g ai/ha to 575 g ai/ha, 275 g ai/ha to 560 g ai/ha, 279 g ai/ha to 1200 g ai/ha, 279 g ai/ha to 1150 g ai/ha, 279 g ai/ha to 1120 g ai/ha, 279 g ai/ha to 1100 g ai/ha, 279 g ai/ha to 600 g ai/ha, or 279 g ai/ha to 558 g ai/ha based on the total amount of the chlormequat chloride in the composition. For example, chlormequat chloride can be applied at a rate from 275 g ai/ha to 1120 g ai/ha and the compound of formula (I) of salt or ester thereof is applied at a rate from 1 g ai/ha to 10 g ai/ha.

The mixtures described herein can be applied in conjunction with one or more other herbicides to control a wider variety of undesirable vegetation. When used in conjunction with other herbicides, the composition can be formulated with the other herbicide or herbicides, tank-mixed with the other herbicide or herbicides or applied sequentially with the other herbicide or herbicides. Some of the herbicides that can be employed in conjunction with the compositions and methods described herein include, but are not limited to: 4-CPA, 4-CPB, 4-CPP, 3,4-DA, 2,4-DB, 3,4-DB, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, bentazon, benthiocarb, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone (e.g., carfentrazone-ethyl), CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon (e.g., cinidon-ethyl), cinmethylin, cinosulfuron, cisanilide, clacyfos, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop (e.g., cyhalofop-butyl), cyperquat, cyprazine, cyprazole, cypromid, daimuron, dalapon, dazomet, delachlor, desmedipham, desmetryn, diallate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethbenzamide, ethalfluralin, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop (e.g., fenoxaprop-P-ethyl), fenoxaprop-P-ethyl +isoxadifen-ethyl, fenoxasulfone, fenquinotrione, fenteracol, fenthiaprop, fentrazamide, fenuron, ferrous sulfate, flamprop, flamprop-M, flazasulfuron, florasulam, fluazifop (e.g., fluazifop-P-butyl), fluazolate, flucarbazone, flucetosulfuron, fluchloralin, flufenacet, flufenican, flufenpyr (e.g., flufenpyr-ethyl), flumetsulam, flumezin, flumiclorac (e.g., flumiclorac-pentyl), flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, fumiclorac, furyloxyfen, halauxifen, halauxifen-methyl, halosafen, halosulfuron (e.g., halosulfuron-methyl), haloxydine, haloxyfop-methyl, haloxyfop-P (e.g., haloxyfop-P-methyl), hexachloroacetone, hexaflurate, hexazinone, imazamethabenz, imazamox, imazapic, imazapyr, imazaquin, imazosulfuron, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lancotrione, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham (e.g., phenmedipham-ethyl), phenobenzuron, phenylmercury acetate, picloram, picolinafen, pinoxaden, piperophos, potassium arsenite, potassium azide, potassium cyanate, pretilachlor, primisulfuron (e.g., primisulfuron-methyl), procyazine, prodiamine, profluazol, profluralin, profoxydim, proglinazine, prohexadione-calcium, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen (e.g., pyraflufen-ethyl), pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thifensulfuron-methyl, thiobencarb, tiafenacil, tiocarbazil, tioclorim, tolpyralate, topramezone, tralkoxydim, triafamone, tri-allate, triasulfuron, triaziflam, tribenuron (e.g., tribenuron-methyl), tricamba, triclopyr, triclopyr esters and salts (e.g., triclopyr choline salt), tridiphane, trietazine, trifloxysulfuron, trifludimoxazin, trifluralin, triflusulfuron, trifop, trifopsime, trihydroxytriazine, trimeturon, tripropindan, tritac, tritosulfuron, vemolate, xylachlor, and salts, choline salts, esters, optically active isomers and mixtures thereof.

The compositions described herein can be used in combination with one or more herbicide safeners, such as AD-67 (MON 4660), benoxacor, benthiocarb, brassinolide, cloquintocet acid, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148, 1-[4-(N-(2-methoxybenzoyl)sulfamoyl)phenyl]-3-methylurea, N-(2-methoxybenzoyl)-4-[(methylaminocarbonyl)amino]benzenesulfonamide and N-phenyl-sulfonylbenzoic acid amides, to enhance their selectivity. The safeners can be used in rice, cereal, corn, or maize settings. The safener can be cloquintocet acid or cloquintocet-mexyl. Cloquintocet is utilized to antagonize harmful effects of the compositions on rice and cereals.

The compositions provided herein can further include one or more agriculturally acceptable adjuvants or carriers. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. The adjuvants or carriers can be solids, such as, for example, dusts, granules, water-dispersible granules, or wettable powders, or liquids, such as, for example, emulsifiable concentrates, solutions, emulsions or suspensions. Additionally, the adjuvants or carriers can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate +urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be used in the compositions and methods described herein include water and organic solvents. Examples of useful organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is useful as a carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

The compositions described herein may further include one or more surface-active agents. Such surface-active agents can be used in both solid and liquid compositions, and can be designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in *McCutcheon's Detergents and Emulsifiers Annual*, MC Publishing Corp., Ridgewood, N.J., 1998 and in *Encyclopedia of Surfactants, Vol. I-III*, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, e.g., methyl esters. These materials, such as vegetable or seed oils and their esters, can be used interchangeably as an agricultural adjuvant, as a liquid carrier or as a surface active agent.

Other additives useful in the compositions provided herein include, but are not limited to, compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

Methods

Methods of using the compositions described herein are also provided. The methods comprise contacting undesirable vegetation with a composition as described herein to prevent the emergence or growth of vegetation, particularly undesirable vegetation. The composition can be applied at an application rate from about 200 grams active ingredient per hectare (g ai/ha) to about 1664 g ai/ha based on the total amount of active ingredients in the composition. Alternatively, the composition can be applied at an application rate from about 250 g ai/ha to about 1,440 g ai/ha based on the total amount of active ingredients in the composition, at an application rate from about 275 g ai/ha to about 1,300 g ai/ha based on the total amount of active ingredients in the composition, or at an application rate from about 280 g ai/ha to about 1,130 g ai/ha based on the total amount of active ingredients in the composition.

In the methods described herein, the components of the mixtures described herein can be applied either separately, sequentially, tank-mixed, or as part of a multipart herbicidal system. Alternatively, the components may be formulated together (e.g., in the same formulation) or separately (e.g., in separate formulations) and applied simultaneously. Also, one or more components may be formulated separately and the components applied sequentially. For example, each component can be formulated separately and the components applied sequentially. The time period between applications can vary, for example 1, 2, 4, 6, 8, 10, or 12 hours or longer or 1, 2, 3, 4, 5, 6, or 7 days or longer.

Methods of application useful in the methods described herein include, but are not limited to, applications to the vegetation or locus thereof, e.g., application to the area adjacent to the vegetation, such as soil and/or water, as well as pre-emergence, post-emergence, and foliar (broadcast, directed, banded, spot, mechanical, over-the-top, or rescue), and in-water applications (emerged and submerged vegetation, broadcast, spot, mechanical, water-injected, granular broadcast, granular spot, shaker bottle, or stream spray) via hand, backpack, machine, tractor, or aerial (airplane and helicopter) application methods.

The compositions described herein can exhibit synergy against a variety of weed types. For example, the combination of the compound of formula (I) or salt or ester thereof plus chlormequat chloride in a ratio of about 1:250 to about 1:50 exhibits greater than about 5, 6, 7, 8, 9, 10, 11, 13, 15, 18, 20, 22, 24, 25, 30, 35, 40, 45, 50, 55, or 60% control compared to the Colby predicted value at 21 days after application (DAA).

The compositions described herein can exhibit synergy as defined by the efficacy values defined above against a variety of weed types or crops, including but not limited to, *Brassica napus napus* (winter rape), *Chenpodium album* L. (common lambsquarters), *Cirsium arvense* (L.) Scop. (Canada thistle), *Galium aparine* L. (catchweed bedstraw), *Kochia scoparia* (L.) Schrad. (kochia), *Lamium purpureum* L. (purple deadnettle), *Matricaria recutita* L. (wild chamomile), *Papaver rhoeas* L. (common poppy), *Salsola tragus* L. (Russian thistle), *Sinapis arvensis* L. (wild mustard), *Stellaria media* (common chickweed), *Veronica persica* Poir. (Persian speedwell), and *Viola tricolor* L. (wild violet).

The methods provided herein can be used to control undesirable vegetation such as grass, broadleaf and sedge weeds, in crops including, but not limited to, direct-seeded, water-seeded and transplanted rice, wheat, durum, barley, millet, oats, rye, sorghum, triticale, corn/maize, teff, fonio, spelt, and canary grass; pseudocereals including, but not limited to, quinoa, amaranth, buckwheat, kañiwa, and pitseed goosefoot; other crops including but not limited to, soybean, cotton, canola, sugar beet, pineapple, oilseed rape; pastures, grasslands, rangelands, and fallowland; turf, tree and vine orchards; plantation crops; aquatics; rights-of-way; and industrial vegetation management (IVM). The compositions and methods provided herein are especially usefule in cereals such as wheat and barley.

In the methods described herein, the compositions can be used to control undesirable vegetation in cereals. Examples of the types of undesirable vegetation that can be controlled in cereals using the methods and compositions described herein include *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Lolium rigidum* m(rigid ryegrass, LOLRI), *Lolium multiflorum* subsp. *Gaudini* (annual ryegrass, LOLMG), *Phalaris minor* Retz. (littleseed canarygrass, PHAMI), *Poa annua* L. (annual bluegrass, POAAN), *Setaria pumila* (Poir.) Roemer & J.A. Schultes (yellow foxtail, SETLU), *Setaria viridis* (L.) Beauv. (green foxtail, SETVI), *Amaranthus retroflexus* (redroot pigweed, AMARE), *Chenopodium album* (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis arvensis* (wild mustard, SINAR), *Stellaria media* (L.) Vill. (common chickweed, STEME), *Veronica hederifolia* (ivy-leaved speedwell, VERHE), *Veronica persica* Poir. (Persian speedwell, VERPE), *Viola arvensis* Murr. (field violet, VIOAR), or *Viola tricolor* L. (wild violet, VIOTR).

In the methods described herein, the compositions can be used to control undesirable vegetation in rice. Examples of the types of undesirable vegetation that can be controlled in rice using the methods and compositions described herein include *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall panicum, PANDI), *Paspalum dilatatum* Poir. (dallisgrass, PASDI), *Cyperus difformis* L. (small-flower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SPCJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Altemanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindemia dubia* (L.) Pennell (low false pimpernel, LIDDU), *Monochoria korsakowii* Regel & Maack (monochoria, MOOKA), *Monochoria vaginalis* (Burm. F.) C. Presl ex Kuhth (monochoria, MOOVA), *Murdannia nudiflora* (L.) Brenan (doveweed, MUDNU), *Polygonum pensylvanicum* L. (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In the methods described herein, the compositions can be used to control undesirable vegetation in range and pasture. Examples of the types of undesirable vegetation that can be controlled in range and pasture using the methods and compositions described herein include *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhom plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G.H. Weber ex Wiggers (dandelion, TAROF), *Trifolium repens* L. (white clover, TRFRE), or *Urtica dioica* L. (common nettle, URTDI).

In the methods described herein, the compositions can be used to control undesirable vegetation in row crops. Examples of the types of undesirable vegetation that can be controlled in row crops using the methods and compositions described herein include *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly sida, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

Other examples of undesirable vegetation that can be controlled using the methods and compounds described herein include *Galium, Veronica, Lamium, Sinapis, Cyperus, Chenpodium, Salsola, Matricaria, Viola, Kochia, Stellaria, Papaver*, and/or *Cirsium*.

The compositions and methods described herein can also be used to control undesirable vegetation in herbicide-tolerant crops including, but not limited to, glyphosate-tolerant-, 5-enolpyruvylshikimate-3-phosphate (EPSP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, phytoene desaturase inhibitor-tolerant-, carotenoid biosynthesis inhibitor-tolerant-, 4-hydroxyphenyl-pyruvate dioxygenase (HPPD) inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant-, and bromoxynil-tolerant-crops (such as, but not limited to, soybean, cotton, canola/oilseed rape, rice, cereals, corn/maize, sorghum, sunflower, sugar beet, sugarcane, turf, wheat, barley, etc.), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil. The compositions and methods may be used in controlling undesirable vegetation in crops possessing multiple or stacked traits conferring tolerance to single or multiple chemistries and/or inhibitors of single or multiple modes of action. The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The described compositions and methods and following examples are for illustrative purposes and are not intended to limit the scope of the claims. Other modifications, uses, or combinations with respect to the compositions and methods described herein will be apparent to a person of ordinary skill in the art without departing from the spirit and scope of the claimed subject matter.

EXAMPLES

Example 1

Evaluation of Post-Emergent Herbicidal Activity

Methodology

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days in a greenhouse with an approximate 14 hour (h) photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of the compound of formula (I) and a second herbicide alone (chlormequat). Weighed amounts of the compound of formula (I) were placed in 25 milliliter (mL) glass vials and dissolved in 4 mL of a 97:3 v/v mixture of acetone and DMSO to obtain concentrated stock solutions. Compound requirements are based upon a 12 mL application volume at a rate of 187 liters per hectare (L/ha). Spray solutions of the second herbicide and compound of formula (I) mixtures were prepared by adding the stock solutions to the appropriate amount of dilution solution to form 12 mL spray solution with active ingredients in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 cm) above average plant canopy. Control plants were sprayed in the same manner with the solvent blank.

The treated plants and control plants were placed in a greenhouse as described above and watered by sub-irrigation to prevent wash-off of the test compounds. After 20-22 days, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

The results are summarized in Table 1.

TABLE 1

Activity of Foliar-Applied Compound I and Chlormequat Chloride Herbicidal Compositions on Weed Control in a Cereal Cropping System 21 Days after Application (DAA)

| Application Rate (g ai/ha) | | BRSNW | | CHEAL | | CIRAR | | GALAP | | KCHSC | | LAMPU | | MATCH | | PAPRH | |
|---|---|---|---|---|---|---|---|---|---|---|---|---|---|---|---|---|---|
| Compound I | Chlormequat Chloride | Obs | Exp | Obs | Exp | Obs | Exp | Obs | Exp | Obs | Exp | Obs | Exp | Obs | Exp | Obs | Exp |
| 2.5 | 0 | 18 | — | 50 | — | 48 | — | 55 | — | 20 | — | 80 | — | 20 | — | 48 | — |
| 5 | 0 | 13 | — | 58 | — | 39 | — | 66 | — | 41 | — | 86 | — | 25 | — | 28 | — |
| 10 | 0 | 13 | — | — | — | 60 | — | 77 | — | 62 | — | 94 | — | 20 | — | 35 | — |
| 0 | 279 | 0 | — | 0 | — | 5 | — | 3 | — | 5 | — | 15 | — | 0 | — | 5 | — |
| 0 | 558 | 3 | — | 3 | — | 5 | — | 5 | — | 5 | — | 15 | — | 0 | — | 5 | — |
| 0 | 1119 | 5 | — | — | — | 10 | — | 20 | — | 7 | — | 30 | — | 27 | — | 7 | — |
| 2.5 | 279 | 23 | 18 | 75 | 50 | 68 | 50 | 60 | 56 | 75 | 24 | 80 | 83 | 50 | 20 | 58 | 50 |
| 2.5 | 558 | 18 | 20 | 78 | 51 | 55 | 50 | 50 | 57 | 68 | 24 | 82 | 83 | 40 | 20 | 73 | 50 |
| 5 | 279 | 33 | 13 | 88 | 58 | 70 | 42 | 68 | 67 | 83 | 44 | 85 | 88 | 60 | 25 | 53 | 32 |
| 5 | 558 | 43 | 15 | 85 | 59 | 65 | 42 | 58 | 68 | 65 | 44 | 85 | 88 | 50 | 25 | 68 | 32 |
| 5 | 1119 | 57 | 17 | — | — | 53 | 45 | 88 | 73 | 70 | 45 | 93 | 90 | 45 | 45 | 72 | 33 |
| 10 | 1119 | 77 | 18 | — | — | 73 | 64 | 92 | 81 | 80 | 64 | 96 | 96 | 40 | 41 | 88 | 39 |

| Application Rate (g ai/ha) | | SASKR | | SINAR | | STEME | | VERPE | | VIOTR | | TRZAS | | HORVS | |
|---|---|---|---|---|---|---|---|---|---|---|---|---|---|---|---|
| Compound I | Chlormequat Chloride | Obs | Exp | Obs | Exp | Obs | Exp | Obs | Exp | Obs | Exp | Obs | Exp | Obs | Exp |
| 2.5 | 0 | 15 | — | 70 | — | 25 | — | 20 | — | 30 | — | 0 | — | 0 | — |
| 5 | 0 | 50 | — | 73 | — | 25 | — | 17 | — | 20 | — | 0 | — | 0 | — |
| 10 | 0 | 67 | — | — | — | 27 | — | 23 | — | 20 | — | — | — | — | — |
| 0 | 279 | 0 | — | 8 | — | 8 | — | 10 | — | 0 | — | 0 | — | 0 | — |
| 0 | 558 | 0 | — | 15 | — | 8 | — | 10 | — | 0 | — | 8 | — | 0 | — |
| 0 | 1119 | 7 | — | — | — | 7 | — | 13 | — | 3 | — | — | — | — | — |
| 2.5 | 279 | 63 | 15 | 85 | 72 | 78 | 31 | 15 | 28 | 28 | 30 | 0 | 0 | 0 | 0 |
| 2.5 | 558 | 58 | 15 | 88 | 75 | 40 | 31 | 10 | 28 | 25 | 30 | 5 | 8 | 0 | 0 |
| 5 | 279 | 70 | 50 | 95 | 75 | 83 | 31 | 33 | 25 | 38 | 20 | 0 | 0 | 0 | 0 |
| 5 | 558 | 58 | 50 | 92 | 77 | 70 | 31 | 15 | 25 | 25 | 20 | 8 | 8 | 0 | 0 |
| 5 | 1119 | 70 | 53 | — | — | 57 | 30 | 27 | 28 | 33 | 23 | — | — | — | — |
| 10 | 1119 | 82 | 69 | — | — | 50 | 32 | 60 | 34 | 43 | 23 | — | — | — | — |

BRSNW = *Brassica napus napus* (winter) (winter rape)
CHEAL = *Chenpodium album* L. (common lambsquarters)
CIRAR = *Cirsium arvense* (L.) Scop. (Canada thistle)
GALAP = *Galium aparine* L. (catchweed bedstraw)
KCHSC = *Kochia scoparia* (L.) Schrad. (kochia)
LAMPU = *Lamium purpureum* L. (purple deadnettle)
MATCH = *Matricaria recutita* L. (wild chamomile)
PAPRH = *Papaver rhoeas* L. (common poppy)
SASKR = *Salsola tragus* L. (Russian thistle)
SINAR = *Sinapis arvensis* L. (wild mustard)
STEME = *Stellaria media* (common chickweed)
VERPE = *Veronica persica* Poir. (Persian speedwell)
VIOTR = *Viola tricolor* L. (wild violet)
TRZAS = *Triticum aestivum* (spring) (spring wheat)
HORVS = *Hordeum vulgare* L. (spring barley)
g ai/ha = grams active ingredient per hectare
Obs = observed value
Exp = expected value as calculated by the Colby equation
Cmpd I = benzyl 4-amino-3-chloro-6-(4-chloro-2-fluoro-3-methoxyphenyl)-5-fluoropyridine-2-carboxylate The compositions and methods of the claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the claims. Further, while only certain representative composition materials and method steps disclosed herein are specifically described, other combinations of the composition materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

What is claimed is:

1. A composition for controlling undesirable vegetation, comprising a herbicidally effective amount of (a) a compound of the formula (I)

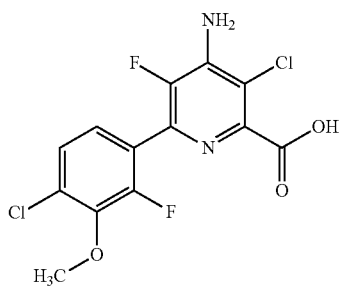

(I)

or an agriculturally acceptable salt or ester thereof and (b) chlormequat chloride, wherein (a) and (b) are present in the composition in a ratio such that the composition exhibits herbicidal synergy.

2. The composition of claim 1, wherein the (a) is a $C_1$-$C_4$ alkyl or $C_7$-$C_{10}$ arylalkyl ester of the compound of formula (I).

3. The composition of claim 1, wherein the (a) is a benzyl ester of the compound of formula (I).

4. The composition of claim 1, wherein the (a) is the compound of formula (I), which is the carboxylic acid.

5. The composition of claim 1, further comprising a herbicide safener.

6. The composition of claim 1, wherein a weight ratio the (a) to (b) is from 1:447 to 112:1.

7. The composition of claim 1, wherein a weight ratio the (a) to (b) is from 1:112 to 28:1.

8. The composition of claim 1, further comprising an agriculturally acceptable adjuvant or carrier.

9. A method of controlling undesirable vegetation, comprising contacting the vegetation or applying to soil or water adjacent thereto with a herbicidal composition comprising a herbicidally effective amount of (a) a compound of the formula (I)

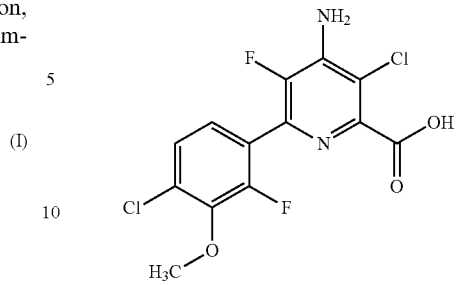

(I)

or an agriculturally acceptable salt or ester thereof and (b) chlormequat chloride, wherein (a) and (b) are present in the composition in a ratio such that the composition exhibits herbicidal synergy.

10. The method of claim 9, wherein the undesirable vegetation is controlled in cereal crops.

11. The method of claim 10, wherein the cereal crop is wheat or barley.

12. The method of claim 9, wherein the (a) is a $C_1$-$C_4$ alkyl or $C_7$-$C_{10}$ arylalkyl ester of the compound of formula (I).

13. The method of claim 9, wherein the (a) is a benzyl ester of the compound of formula (I).

14. The method of claim 9, wherein the (a) is the compound of formula (I), which is the carboxylic acid.

15. The method of claim 9, wherein the composition further comprises a safener.

16. The method of claim 9, wherein a weight ratio of the (a) to (b) is from 1:447 to 112:1.

17. The method of claim 9, wherein a weight ratio of the (a) to (b) is from 1:112 to 28:1.

18. The method of claim 9, further comprising an agriculturally acceptable adjuvant or carrier.

19. The method of claim 9, wherein the undesirable vegetation is controlled in glyphosate-tolerant-, glufosinate-tolerant-, dicamba-tolerant-, phenoxy auxin-tolerant-, pyridyloxy auxin-tolerant-, aryloxyphenoxypropionate-tolerant-, acetyl CoA carboxylase (ACCase) inhibitor-tolerant-, imidazolinone-tolerant-, acetolactate synthase (ALS) inhibitor-tolerant-, 4-hydroxyphenyl-pyruvate dioxygenase (HPPD) inhibitor-tolerant-, protoporphyrinogen oxidase (PPO) inhibitor-tolerant-, triazine-tolerant-, and bromoxynil-tolerant-crops possessing single, multiple or stacked traits conferring tolerance to single or multiple chemistries and/or single or multiple modes of action.

* * * * *